(12) United States Patent
Shi et al.

(10) Patent No.: US 6,287,821 B1
(45) Date of Patent: Sep. 11, 2001

(54) NUCLEOTIDE ANALOGUES WITH 3'-PRO-FLUORESCENT FLUOROPHORES IN NUCLEIC ACID SEQUENCE ANALYSIS

(75) Inventors: Jufang Shi, Naperville, IL (US); Michael T. Boyce-Jacino, Finksburg; Phillip Goelet, Reisterstown, both of MD (US)

(73) Assignee: Orchid BioSciences, Inc., Princeton, NJ (US)

( * ) Notice: Subject to any disclaimer, the term of this patent is extended or adjusted under 35 U.S.C. 154(b) by 0 days.

(21) Appl. No.: 09/095,648

(22) Filed: Jun. 11, 1998

(51) Int. Cl.[7] ............................................. C12P 19/34
(52) U.S. Cl. ........................... 435/91.2; 435/6; 536/26.6
(58) Field of Search ...................... 435/6, 91.2; 536/266

(56) References Cited

FOREIGN PATENT DOCUMENTS

0745688 * 12/1996 (EP) .

OTHER PUBLICATIONS

Sanger, et al., DNA sequencing with chain–terminating inhibitors, *Proc. Natl. Acad. Sci.* vol. 74 pp. 54, (1977).*

* cited by examiner

*Primary Examiner*—Scott W. Houtteman
(74) *Attorney, Agent, or Firm*—David A. Kalow, Esq.; William D. Schmidt, Esq.; Kalow & Springut LLP

(57) ABSTRACT

The invention concerns a novel class of 3'-modified, pro-fluorescent nucleotides. The invention also pertains to methods for using such nucleotides.

49 Claims, 4 Drawing Sheets

Figure 1:
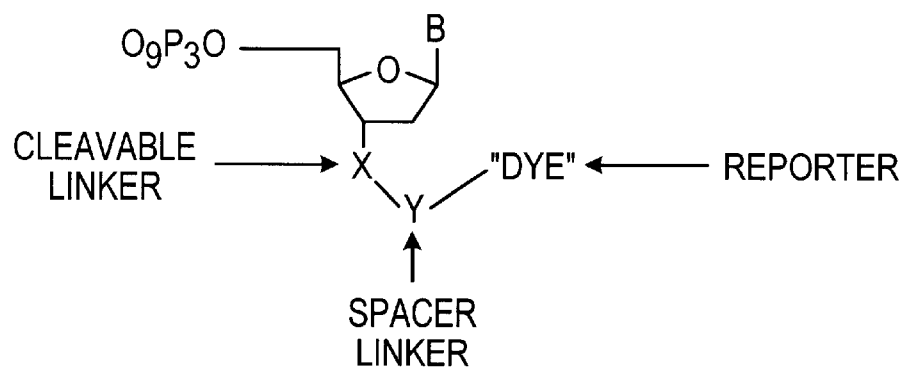

X = NH-C(O)-, O-C(O)-, -OPO3, CH2CO;
Y = -(NH-CO)-n, -(OCH2-CH2)n;
REPORTER = DYES, OR COLORMETRIC & FLUOROMETRIC SUBSTRATES.

NUCLEOTIDE ANALOGUES WITH 3'-PRO-FLUORESCENT FLUOROPHORES IN NUCLEIC ACID SEQUENCE ANALYSIS

FIELD OF THE INVENTION

The present invention describes the design and synthesis of a class of internally quenched, fluorogenic substrates for nucleic acid polymerases. More specifically, the present invention describes the design and synthesis of nucleotide analogues with 3'-pro-fluorescent fluorophores (3'-PF-ddNTPs), which are useful as detectors of specific enzyme activity, as well as terminator and non-terminator substrates for nucleic acid polymerases. Methods of the present invention include the use of the nucleotides of the present invention in nucleic acid sequence analysis, as well as the kinetic analysis of polymerase activity.

BACKGROUND OF THE INVENTION

I. Sequence Analysis Using Dideoxynucleotides

Chain terminating 2',3'-dideoxynucleotide triphosphates (ddNTPs) are widely used in nucleic acid sequencing technology (Sanger, et al., *Proc. Nat. Acad. Sci.(USA)*, 74:5463 (1977)). Traditionally, Sanger sequencing involves the polymerase-mediated incorporation of a dideoxynucleotide onto the 3' end of an elongating DNA chain. Incorporation of a dideoxynucleotide results in chain termination, as dideoxynucleotides lack a 3'-OH suitable for further elongation. Methods for Sanger sequencing are disclosed, for example, in J. Sambrook, et al., *Molecular Cloning, A Laboratory Manual*, 2nd Edition, Cold Spring Harbor Press, Cold Spring Harbor, N.Y. (1989), and in J. W. Zyskind, et al., *Recombinant DNA Laboratory Manual*, Academic Press, Inc., New York (1988)), both herein incorporated by reference.

In Sanger sequencing, four reactions are typically performed for each polynucleotide to be sequenced. Each reaction contains a DNA template, an oligonucleotide primer, and a mixture of all four deoxynucleotide triphosphates (dNTPs). In addition, each reaction contains one of the four ddNTPs. Either the oligonucleotide primer or the ddNTPs are radiolabeled. The reaction results in a series of radioactivly labeled, prematurely terminated extension reaction products, which are then separated on individual lanes of a high resolution polyacrylamide gel. The gel is then dried and exposed to photographic or x-ray film to record the results for analysis. The procedure is time-consuming, requires significant technical expertise, and involves the use of both radioactive and neurotoxic materials.

The original chain termination or Sanger method has been improved in several ways, and serves as the basis for all currently available automated DNA sequencing machines. See, e.g., Sanger et al., *J. Mol. Biol.* 143:161–78 (1980); Schreier et al., *J. Mol. Biol.* 129:169–72 (1979); Smith et al., *Nucleic Acids Res.* 13:2399–2412 (1985); Smith et al., *Nature* 321:674–79 (1987); Smith et al., U.S. Pat. No. 5,171,534; Prober et al., *Science* 238:336–41 (1987); Section II, *Meth. Enzymol.* 155:51–334 (1987); Church et al., *Science* 240:185–88 (1988); Swerdlow et al., *Nucleic Acids Res.* 18:1415–19 (1989); Ruiz-Martinez et al., *Anal. Chem.* 65:2851–58 (1993); Studier, *Proc. Natl. Acad. Sci. (USA)* 86:6917–21 (1989); Kieleczawa et al., *Science* 258:1787–91; and Connell et al., *BioTechnigues* 5:342–348 (1987)).

II. Fluorescently Labeled Nucleotides

In an effort to overcome some of the obvious drawbacks and limitations of Sanger sequencing, fluorescently labeled dideoxynucleotides have been developed for use in nucleic acid sequencing (Bergstrom et al., *J. Am. Chem. Soc.*, 98:1587-(1976); Hobbs et al., (U.S. Pat. No. 5,047,519; Ward et al., U.S. Pat. No. 5,449,767). In these fluorescently labeled ddNTPs, the dye is conjugated to the base. The use of four distinguishably labeled ddNTPs has further allowed the process to be condensed to a single reaction, run on a single lane on a gel (L. G. Lee, et al., *Nucleic Acids Res.*, 20:2471–2483 (1992)). This has facilitated the automation of DNA sequencing.

Nevertheless, the use of fluorescent labels in nucleic acid sequence analysis also has its drawbacks. Fluorescent labels are less sensitive than radioactive labels. Consequently, either a greater amount of material must be used to achieve a detectable signal or the template DNA must be amplified by a method such as the Polymerase Chain Reaction (PCR). In addition, Sanger sequencing with fluorescently labeled ddNTPs retains the drawbacks inherent in polyacrylamide gel use. That is, it is time-consuming, requires significant technical expertise, and utilizes acrylamide (a neurotoxin).

III. 3'-Substituted Nucleotides

Nucleotides substituted at the 3' position of the sugar have also been reported to function as terminators for polymerases. Substitutions reported to efficiently terminate DNA synthesis include azido (H. Mitsuya, et al., *Proc. Natl. Acad. Sci USA*, 83:1191–1915 (1986)), mercapto (A.A. Yuzhakov, et al., *FEBS Lett.*, 306:185–188 (1992)), amino (M. Herrlein, et al., *Helvetica Chimca Acta*, 77:586–596 (1994)), and fluoro groups (Z. G. Chidgeavadze, et al., *FEBS Lett.*, 183:275–278 (1985)). In addition, a class of nucleotides with 3'-conjugated reporters has been shown to function as dye terminators (B. Canard et al., *Gene*, 148:1–6 (1994); M. L. Metzker, et al., *Nucleic Acids Res.*, 22:4259–4267 (1994); A. V. Azhayev et al., *Nucleic Acids Res.*, 6:625–643 (1979); K. Faulstich et al., *Bioorganic & Med. Chem. Lett.*, 4:1975–1978 (1994)).

IV. Fluorescence Quenching

Fluorescent dyes are sensitive to their environment. Free dyes give the maximum quantum yield, whereas conjugated dyes are typically quenched to some degree. Extrinsic quenchers, the most ubiquitous of which are paramagnetic species (such as $O_2$) and heavy atoms (such as iodide), reduce fluorescence quantum yields in a concentration-dependent manner. Many fluorophores are also quenched by protein. Examples are NBD, fluorescein and BODIPY dyes, in which the effect is apparently due to charge-transfer interactions with aromatic amino acid residues. (*Biophys. J.* 69:716 (1995); *Biochemistry* 16:5150 (1977); *Immunochemistry* 14:533 (1977)). Consequently, antibodies raised against these fluorophores are effective and highly specific fluorescence quenchers.

Besides extrinsic quenching mechanisms, many other environmental factors influence fluorescence properties. The four most common are solvent polarity, the proximity and concentrations of quenching species, the pH of the aqueous medium, and the binding of a probe to its target (such as DNA stain dyes). However, these quenching mechanisms are not readily applicable to the design of dye terminators. Common causes of the fluorescence quenching seen in dye conjugates includes dipole-dipole interactions, hydrophobic interactions and charge/energy transfer.

V. Conclusions

It would be desirable to develop a fluorogenic system for detecting and measuring polymerase activity, where production of a fluorescent species correlates with the activity of a polymerase or other enzyme. The present invention meets this need and more, by providing a class of pro-fluorescent nucleotides that release a free fluorophore upon polymerase-mediated incorporation of the nucleotide. Thus, the invention allows for determination of base incorporation in the presence of unincorporated nucleotides. In doing so, in certain embodiments the present invention also provides a novel and highly sensitive means for amplifying the signal produced as a result of that incorporation. Thus, the present invention provides a class of reagents useful in a variety of applications, including kinetic studies, polymerase reaction monitoring, and non-gel-based sequence determination methods.

SUMMARY OF THE INVENTION

The present invention provides a novel class of fluorogenic, pro-fluorescent nucleotides (3'-PF-ddNTPs) that may act as either terminator or non-terminator substrates in nucleic acid polymerase reactions or other enzymatic reactions, depending upon the particular combination of polymerase, other enzymes, and 3'-pro-fluorescent nucleotide (3'-PF-ddNTP) species utilized. Owing to the fluorogenic nature of 3'-PF-ddNTPs, reporter release correlates with polymerase activity and is detectable in the presence of unutilized or unincorporated 3'-PF-ddNTPs. In embodiments where an enzyme with a 3'→5' exonuclease activity is used, the invention further provides a novel means for amplifying the signal generated without further amplifying the target polynucleotide. 3'-PF-ddNTPs are useful, therefore, in numerous types of in vitro and in vivo nucleic acid polymerase and other enzymatic reactions. Further, 3'-PF-ddNTP may be readily applied to either solution-phase or solid-phase assays. Particular uses include non-gel-based sequence analysis, PCR reaction monitoring, hybridization detection, and real-time kinetic measurements of nucleic acid polymerase reactions.

In detail, the invention provides a compound of formula N-L1-L2-Reporter, where N is a nucleotide; L1 represents a cleavable linking group, such that one end of the cleavable linking group is attached to the 3' position of said nucleotide; L2 represents a spacer linking group; and Reporter represents a chromophore or a pro-fluorescent fluorophore, particularly where the compound itself exhibits a low fluorescence (profluorescent structure) and the reporter fluoresces more when it is cleaved from the rest of the compound. The invention is particularly concerned with embodiments wherein L is at least one moiety selected from the group consisting of: NH—C(O)—, NH—C(S)—, CH2CO, O—C(O)—, or —OPO3—; and/or L2 is at least one moiety selected from the group consisting of: —(NH—CO)n— or —(OCH2—CH2)n; and/or Reporter is selected from the group fluorescein, rhodamine, coumarin, acridine, ELF, and related derivatives which when coupled to the compound are less fluorescent than when not coupled to the compound.

The invention further provides a method for determining the identity of a nucleotide at at least one preselected site in a target polynucleotide (such as DNA or RNA), comprising the steps of:

(a) incubating a target polynucleotide in the presence of at least one 3'–5' exonuclease-resistant primer oligonucleotide (especially a phosphorothioated oligonucleotide) having a sequence complementary to a sequence immediately 3' to a preselected site of the target polynucleotide, the incubation being under conditions sufficient to permit the primer oligonucleotide to hybridize to the target oligonucleotide and to thereby form a hybridized product;

(b) further incubating the hybridized product in the presence of a mixture comprising a polymerase and at least one pro-fluorescent nucleotide species, particularly 3'-PF-ddNTP species; the incubation being under conditions sufficient to permit the polymerase-mediated template-dependant addition of the nucleotide species onto the 3'-terminus of the hybridized primer oligonucleotide;

(c) permitting the polymerase to mediate the template-dependant addition of a pro-fluorescent nucleotide species onto the 3'-terminus of the hybridized primer oligonucleotide, the addition being additionally dependant on the mixture containing a pro-fluorescent nucleotide species that is complementary to a nucleotide present at the preselected site;

(d) permitting the enzymatic hydrolysis of a reporter from the complementary pro-fluorescent nucleotide species;

(e) determining the identity of the nucleotide at the preselected site from the identity of the reporter.

The invention further provides methods additionally comprising multiple iterations of steps (b), (c), and (d), prior to step (e).

The invention concerns embodiments wherein the mixture in step (b) above contains one or more species of terminator or non-terminator pro-fluorescent nucleotide species.

The invention also concerns embodiments as described above wherein either the target polynucleotide or a multiplicity of primer oligonucleotides are spatially arranged in an array, such as when affixed to a solid support, preferably where each element of the array is at least 1 μM in diameter and the array contains at least one element.

The invention also provides a method wherein the hydrolysis of the reporter from the pro-fluorescent nucleotide substantially unquenches the fluorescence of the reporter.

The invention also concerns embodiments as described above wherein in step (d) the enzymatic hydrolysis of the reporter is accomplished by the polymerase.

The invention also concerns embodiments as described above, wherein step (d) is preceded by a washing step and the enzymatic hydrolysis of the reporter is accomplished by an enzyme with an activity selected from the group: esterase, alkaline phosphatase, or glycosidase.

The invention also concerns embodiments as described above wherein the polymerase is a T7, a modified T7, a T5, a Klenow Class DNA polymerase, Taq polymerase or Taq-related polymerase.

The invention also concerns embodiments as described above wherein the enzymatic hydrolysis of the label in step (d) and the exonuclease-mediated removal in step (e) are accomplished by the polymerase and the polymerase is a T5, a T7, or a modified T7 DNA polymerase.

The invention also concerns embodiments as described above wherein in step (f) the identity is determined in the presence of unreacted or unincorporated pro-fluorescent nucleotides.

The invention also provides method for determining the nucleic acid sequence of a target polynucleotide comprising the steps of:

(a) incubating a target polynucleotide in the presence of at least one primer oligonucleotide, the primer oligonucleotide having a sequence complementary to a sequence immediately 3' to a first preselected site of the target polynucleotide, the incubation being under conditions sufficient to permit the primer oligonucleotide to hybridize to the target oligonucleotide and to thereby form a hybridized product;

(b) further incubating the hybridized product in the presence of a mixture comprising a polymerase and at least one terminator pro-fluorescent nucleotide species; the incubation being under conditions sufficient to permit the polymerase-mediated template-dependant addition of the terminator pro-fluorescent nucleotide species onto the 3'-terminus of the hybridized primer oligonucleotide;

(c) permitting the polymerase to mediate the template-dependant 3' extension of the primer oligonucleotide by one terminator pro-fluorescent nucleotide species, the extension being additionally dependant on the mixture containing a terminator pro-fluorescent nucleotide species that is complementary to a nucleotide of the target polynucleotide present at the preselected site;

(d) permitting the enzymatic hydrolysis of a reporter from the complementary nucleotide species, thereby restoring a 3' end suitable for the polymerase-mediated template-dependant extension of a the primer oligonucleotide by an additional terminator pro-fluorescent nucleotide species;

(e) determining the identity of the nucleotide at the preselected site from the identity of the hydrolyzed reporter;

(f) performing multiple iterations of steps (b) through (e), thereby in each iteration sequentially extending the primer oligonucleotide by one terminator pro-fluorescent nucleotide, and determining the identity of a next adjacent nucleotide of the target polynucleotide from the identity of the hydrolyzed reporter.

The invention is particularly concerned with variations of the above-described embodiment wherein the hydrolyzed reporter is removed by washing between each iteration of steps (b) through (e).

The invention also concerns variations of the above-described embodiment wherein in step (e) the identity is determined in the presence of unreacted or unincorporated pro-fluorescent nucleotides.

The invention also concerns variations of the above-described embodiment wherein in step (d) the hydrolysis of the reporter substantially unquenches the fluorescence of the reporter.

The invention also concerns variations of the above-described embodiment wherein the target polynucleotide is either a DNA molecule.

The invention also concerns variations of the above-described embodiment wherein the target polynucleotide is an RNA molecule and the polymerase is a reverse transcriptase.

The invention also concerns variations of the above-described embodiment wherein in step (d) the enzymatic hydrolysis of the label is accomplished by the polymerase.

The invention also concerns variations of the above-described embodiment wherein in step (d) the enzymatic hydrolysis of the label is accomplished by an enzyme with an activity selected from the group: esterase, alkaline phosphatase, or glycosidase.

The invention also concerns variations of the above-described embodiment wherein the terminator pro-fluorescent nucleotide species are 3'-PF-ddNTP species.

The invention also concerns variations of the above-described embodiment wherein the polymerase is a T7, a modified T7, a T5, or a Klenow Class DNA polymerase.

BRIEF DESCRIPTION OF THE FIGS.

FIG. 1 provides a diagrammatic representation of a generic 3'-PF-ddNTP.

Figure 2:
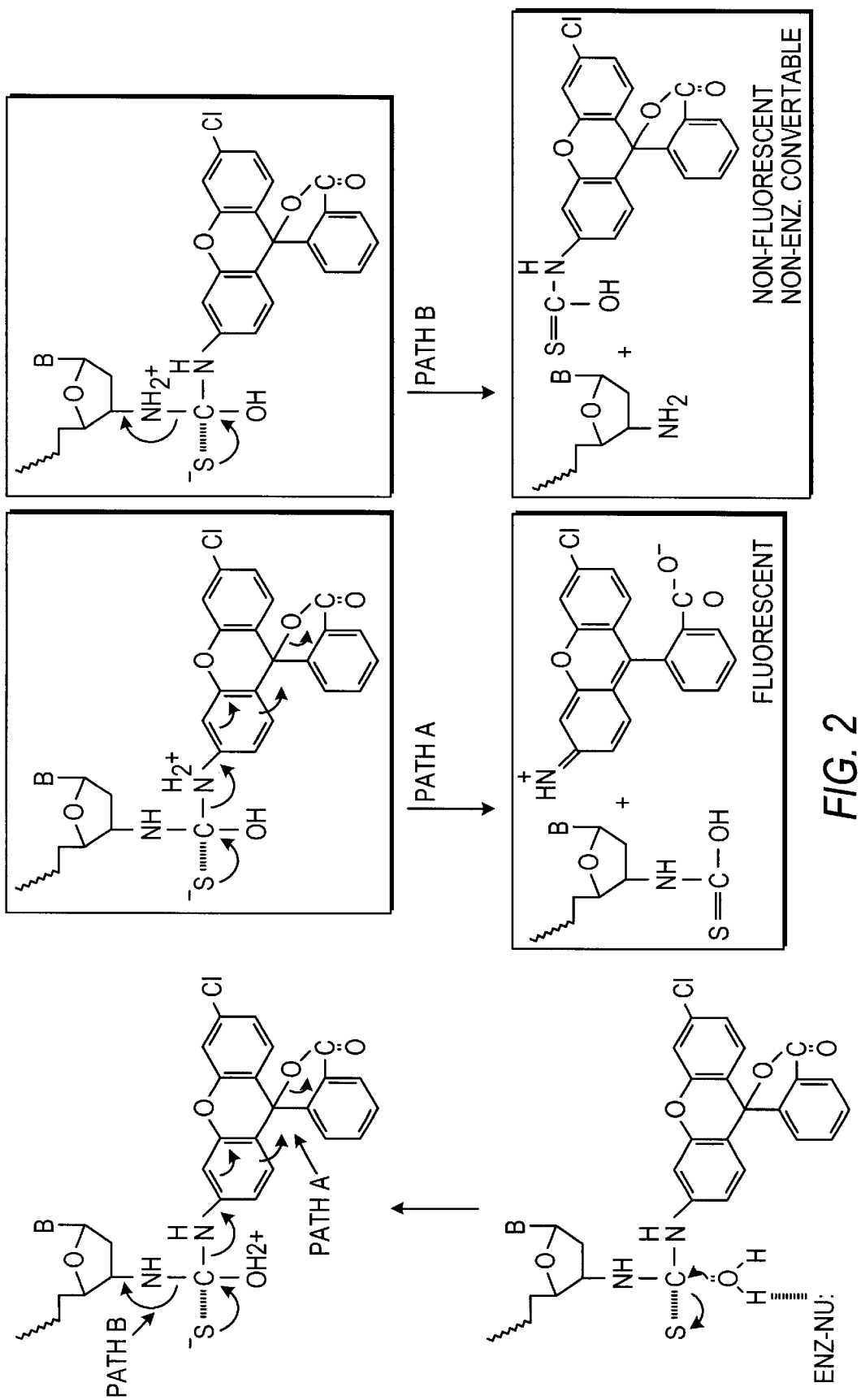

FIG. 2 provides a diagrammatic representation of the hydrolysis of a 3' thiourea-linked pro-fluorescent nucleotide. Two cleavage pathways are noted.

Figure 3:
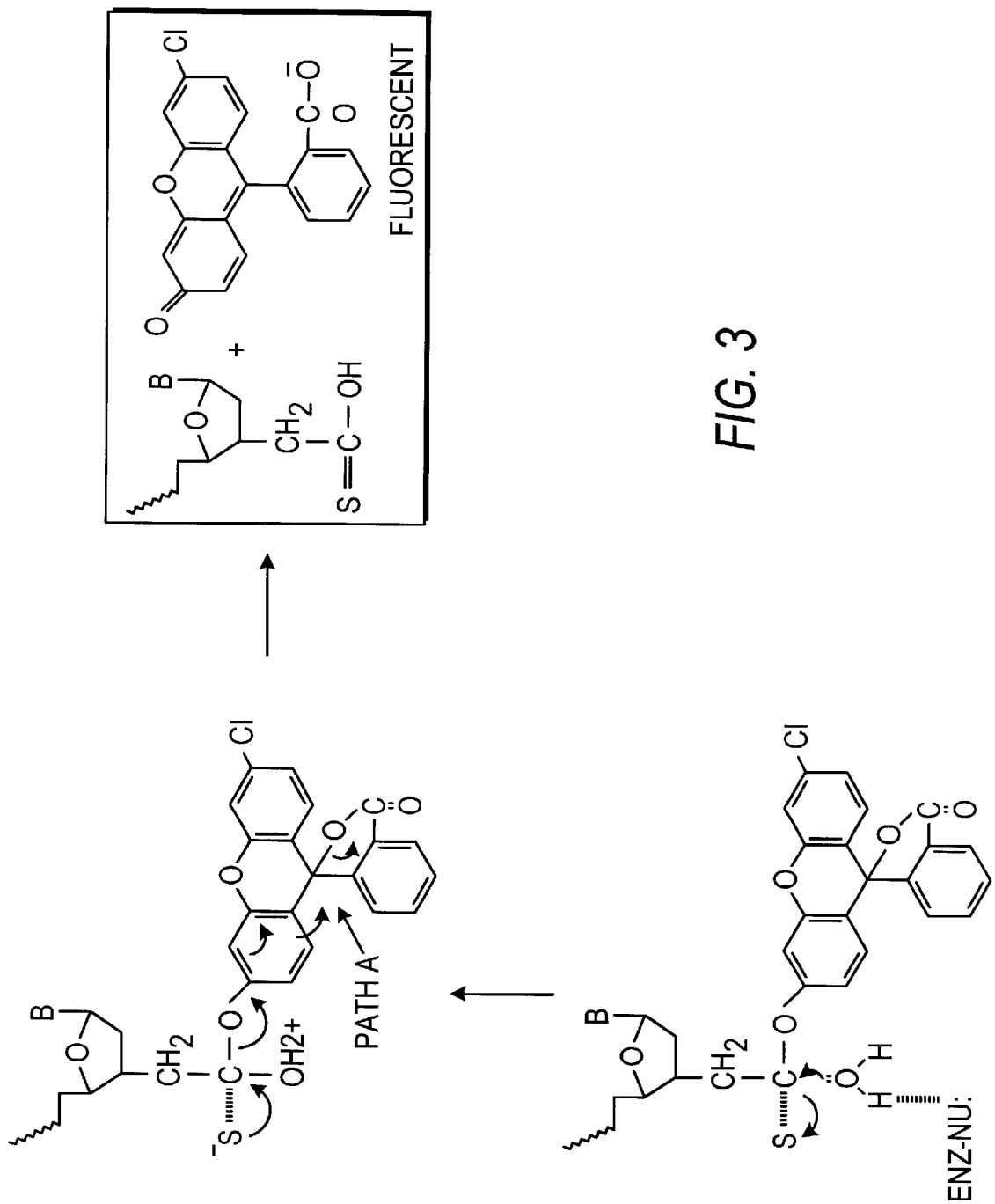

FIG. 3 provides a diagrammatic representation of the hydrolysis of a pro-fluorescent nucleotide with a preferred cleavage pathway resulting in the production of a fluorescent product.

Figure 4:
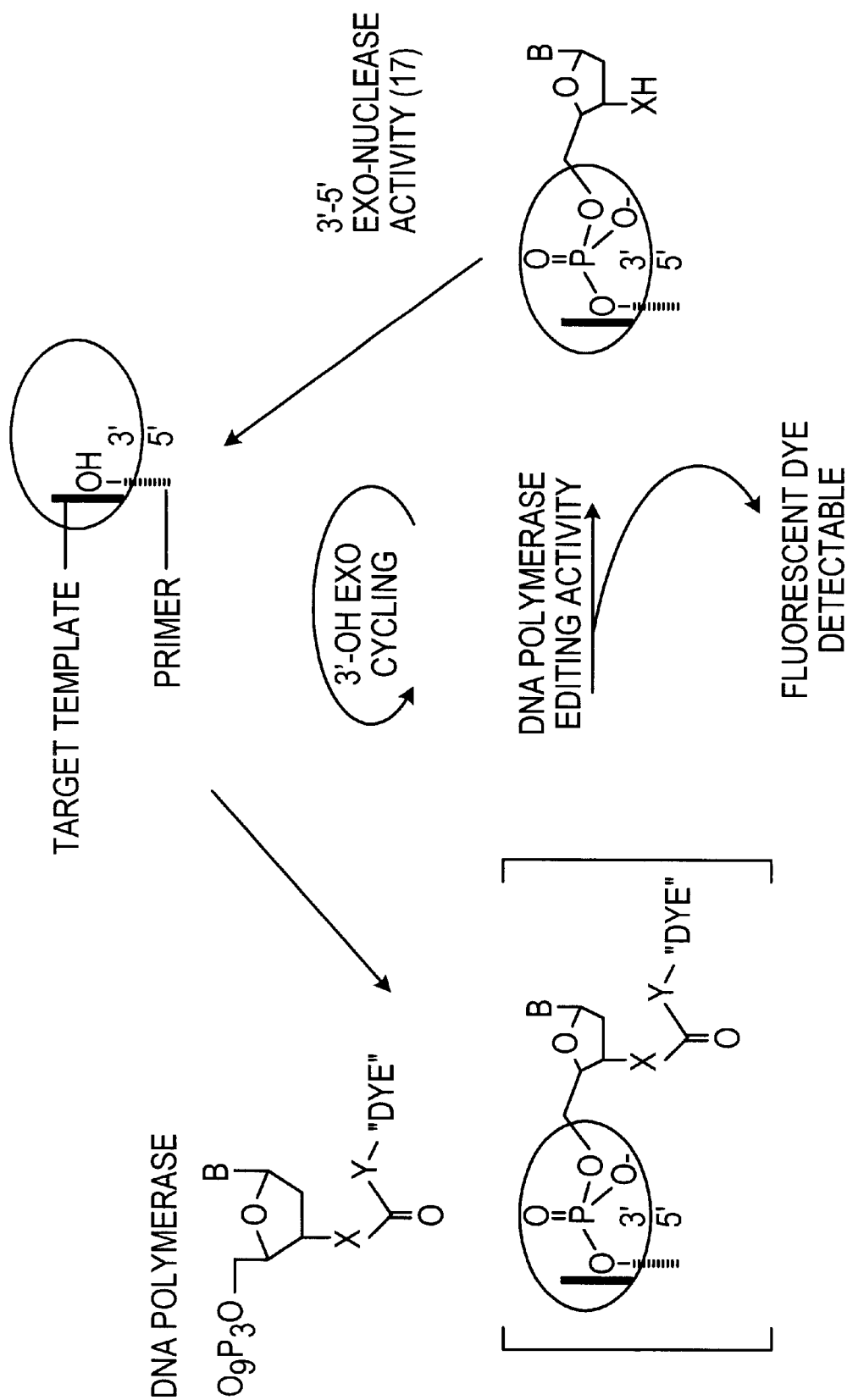

FIG. 4 provides a diagrammatic representation of the 3'-OH Exo Cycle.

DETAILED DESCRIPTION OF THE INVENTION

Recently, it has been reported that 3'-esterified 2'-deoxynucleotide 5'-triphosphates are "false" chain-terminators, since several DNA polymerases, including human immunodeficiency virus reverse transcriptase, can incorporate them into DNA, cleave off their 3'-esterified modification, and use the resulting 3'-OH in further extension reactions (B. Canard, et al., *Proc. Natl. Acad. Sci USA*, 92:10859–10863 (1995)). Reporter groups conjugated in the 3'-position through amide or thiourea bonds can also be incorporated and cleaved to restore a 3'-OH. It is reasoned that the polymerase-bound 3' end of the DNA lies in the vicinity of a powerful nucleophilic group in the active site involved either in polymerization or in 3'-substituent removal. This suggestion is in accordance with crystallographic data for several DNA polymerases (D. L. Ollis et al., *Nature* (London) 313:762–766 (1985); L. A. Kohlstaedt et al., *Science* 256:1783–1790 (1992); R. Sousa et al., *Science* 364:593–599 (1993); J. F. Davies et al., *Cell* 76:1123–1133 (1994); H. Pelletier et al., *Science* 264:1891–1903 (1994)). This suggests that previous observations of read-through and quenching (T. V. Kutateladze et al., *Febs Lett.* 207:205–212 (1986); Z. G. Chidgeavadze et al., *Nucl. Acids Res.*, 12:1671–1686 (1984); Z. G. Chidgeavadze et al., *Biochim. Biophys. Acta*, 868:145–152 (1986)) may, in fact, be explained as a quantitative removal of the fluorescent reporter upon enzymatic chain extension.

The present invention stems, in part, from the realization that a class of nucleotides may be constructed that are fluorogenic (pro-fluorescent) in nature. Fluorophore quenching can be intentionally engineered into a fluorescently labeled nucleotide through structural modification. For example, conversion of the prototypic 3'- and 6'-hydroxyl groups of fluorescein to acetate esters yields fluorescein diacetate. This derivatization causes fluorescein to adopt the non-fluorescent lactone configuration; cleavage of the acetate by esterase under appropriate pH conditions releases fluorescent anionic fluorescein. Fluorogenic substrates for other hydrolytic enzymes are created by replacing acetates with other appropriate functional groups such as phosphate, sulfate, ether or other esters. Further, a variety of fluorogenic substrates are metabolized to products that have longer-wavelength excitation or emission spectra. These fluorescent products can typically be quantitated in the presence of unreacted substrate using a fluorometer or a fluorescence microplate reader, which facilitates high-throughput analysis.

Another mechanism utilizing structural modification to regulate fluorescence is through steric hindrance. An example is the fluorophore ELF-97, in which fluorescence can be programmed by the altering substituents on the oxygen. The steric hindrance between the substituents and the lone pair electron of the nitrogen, force the non-planarity of the ring system. This non-planarity distorts the π-system for electron delocalization, the π-electron can not be excited, and there is no emission as a consequence.

The use of a fluorogenic oligonucleotide has been applied to the detection of a PCR product (S. J. Faas et al., *Tissue Antigens* 48:97–112 (1996)). The method of Faas et al. relies on a doubly labeled fluorogenic oligonucleotide that hybridizes internal to a PCR product. The doubly labeled oligonucleotide is constructed such that it contains a fluorophore at one end and a quenching moiety at the other end. During the course of a PCR reaction, the 5'→3' exonuclease activity of Taq polymerase digests the doubly-labeled oligonucleotide, separating the fluorescently labeled nucleotide from the quenched species. The assay, however, is not suited to microsequencing systems or other non-PCR polymerase reactions. Further, in Faas et al., the fluorescent species is a fluorescently labeled nucleotide, rather than a free fluorophore. In addition, only a single fluorescent molecule is released for each strand that is synthesized. Lastly, the assay requires the synthesis of a complex doubly-labeled fluorogenic oligonucleotide probe that lies internal to the PCR product. Consequently, a different doubly-labeled fluorogenic probe must be designed for each new amplification product. A system that is more generally applicable to a variety of polymerase reactions would be more desirable.

Canard, et al., (Canard et al. EP 0745688) suggests the possibility of using 3'-fluorescently-labeled, false-terminator nucleotides in polymerase reactions. Canard further suggests the possibility of differentiating intact false-terminator nucleotides from released label based on a Stokes shift in the emission spectra. However, this would require a complex spectral analysis to measure released fluorophore in the presence of intact false-terminator nucleotides. A simple fluorescence/no fluorescence system utilizing a fluorogenic substrate or based on fluorescence quenching would be more desirable. Further, Canard et al does not suggest the possibility of producing increased fluorescence output by using pro-fluorescent nucleotides in conjunction with exonuclease-resistant oligonucleotides and an enzyme with 3'→5' exonuclease activity.

Thus, in the present invention, hydrolyzable pro-fluorescent nucleotides (3'-PF-ddNTPs) are provided. These nucleotides, in their pro-fluorescent form, are utilized by a DNA polymerase or other enzyme, whereupon the hydrolytic property of the enzyme edits the nascent 3'-end of the 3'-PF-nucleotide. The present invention also provides methods that utilize the unique features of such 3'-PF-ddNTPs.

I. 3'-PF-ddNTPs of the Present Invention

All of the claimed compounds of the present invention may be synthesized from known, conventional, or commercially available starting materials using known or conventional synthesis methods. Three elements comprise 3'-PF-ddNTPs: A nucleotide, a cleavable linker, and a reporter. Preferably, a spacer linker is additionally positioned between the cleavable linker and the reporter (FIG. 1). Important to the design of 3'-PF-ddNTPs, are the best possible combination of cleavable linker, spacer linker and reporter dye.

A. Nucleotides

The term "nucleotide" as used herein refers to ribonucleotides, deoxyribonucleotides, dideoxynucleotides, acyclic derivatives of nucleotides, and functional equivalents thereof, of any phosphorylation state. Functional equivalents of nucleotides are those that may be functionally substituted for any of the standard ribonucleotides or deoxyribonucleotides in an a polymerase or other enzymatic reaction as, for example, in an amplification or primer extension method. Functional equivalents of nucleotides are also those that may be formed into a polynucleotide that retains the ability to hybridize in a sequence specific manner to a target polynucleotide.

B. Cleavable Linker

The cleavable linker is preferably attached at one end to the 3' position of the nucleotide and at the other end to a spacer linker. However, the cleavable linker may alternatively be attached directly to a reporter. Cleavable linkers are substrates for the 3' enzymatic editing performed by certain enzymes, particularly certain polymerases. Examples of preferred polymerase enzymes with 3' enzymatic editing activity include T5 polymerase, Klenow polymerase, and T7 polymerase. In certain molecules of the present invention, cleavable linkers are substrates for hydrolytic reactions catalyzed by enzymes, such as esterases, phosphatases, or alkaline phosphatases. Some cleavable linkers will be substrates for 3' enzymatic editing performed by more than one of the above. Examples of preferred cleavable linkers include NH—C(O)—, O—C(O)—, —OPO$_3$—, or CH$_2$CO groups.

In addition to acting as a substrate for 3' enzymatic editing, the cleavable linker, in concert with the remainder of the 3'-PF-ddNTP, preferably contributes to fluorescence quenching in the intact 3'-PF-ddNTP. However, since the cleavable linker is positioned in the vicinity of the enzyme's active site, the choice of cleavable linker is guided not only by the desire to achieve maximal quenching of the pro-fluorescent substrate, but also by the need to be hydrolyzable by the desired DNA polymerase, enzyme, or enzyme combination.

During hydrolysis, nucleophilic attack transforms the SP2 carbon of a cleavable linker (preferably comprising a thiourea, amide, or ester group) into a transition state tetrahedral carbon (FIG. 2). In the transition state, two pathways (path a and path b) lead to cleavage. Generally, only one of these pathways leads to the production of a fluorescent product. Thus, these two pathways are regulated depending on the format of detection and the desired application. According to the methods of the present invention it is generally preferred for release of the fluorescent label to directly correlate with polymerase activity. Consequently, 3'-PF-ddNTPs are preferably constructed to allow one pathway to predominate. For example, when CH$_2$CO is used as a linker between the fluorophore and the sugar, the preferred pathway is release of the fluorescent product (FIGS. 2 and 3). Consequently, 3'-PF-ddNTPs incorporating a methylene amide cleavable linker are examples of highly preferred molecules of the present invention.

The synthesis chemistry for thiourea linked molecules is much simpler than that required for the synthesis of methylene amide linked molecules. Thiourea-linked molecules are therefore particularly preferred molecules of the present invention, due in part to the known edibility of the related molecules by polymerases and the feasibility of the synthesis of the isothiocyanate intermediates by means known in the art. Furthermore, the semi-thiourea or semi-urea reaction products are chemically unstable and undergo self decomposition to corresponding fluorescent compounds. Thus, both path a and b lead to the same fluorescence and correlate with the polymerization event.

Phosphate esters are useful as stable linkers, particularly in the design of terminator pro-fluorescent nucleotide species. A number of phosphate esters of nucleoside 5'-triphosphates are substrates for DNA dependent RNA polymerases (W. J. Smagowicz et al., *Biochemistry*, 20:5538–5546 (1981); A. Cvekel et al., *Int. J. Biol. Macromol.*, 11:33–38 (1989)). However, 3'-phosphates are potent blockers of DNA polymerases (A. Kornberg et al., In: *DNA Replication*, A. Kornberg & T. A. Baker eds. (Freeman, San Francisco), pp 408, 403–437 (1992)). This may be the result of the fact that a phosphate can not receive nucleophilic attack unless it is precisely ligated to a metal ion.

C. Spacer Linker

In those embodiments where a fluorophore is used as a reporter molecule, the spacer linker, in concert with the remainder of the 3'-PF-ddNTP, preferably interacts with the dye moiety to substantially quench the fluorescent yield of the fluorophore. The spacer linker is preferably attached to the cleavable linker at one end and to the reporter molecule at the other end. The length of the spacer linker can have a dramatic effect on fluorescence quenching in intact 3'-PF-ddNPTs (see for example, K. Faulstich et al., *Bioorganic & Med. Chem. Lett.*, 4:1975–1978 (1994)). Examples of spacer linkers include —(NH—CO)$_n$— or —(OCH$_2$—CH$_2$)$_n$ groups, individually or in combination, where n is from 1 to 10. Preferred lengths of spacer linkers are where n is from 1 to 4, with a highly preferred range of 1 to 2.

In addition to affecting fluorophore quenching, differences in the length of linkers in 3'-esterified modifications can show dramatic differences in the steric hindrance resulting from a bulky reporter group. There is also evidence that esters (COO) are oriented differently from amides (CONH) in the ternary complex of a DNA duplex, a polymerase, and incoming nucleotide triphosphates. However, in 3'-PF-ddNTPs utilizing amide or thiourea-based cleavable linkers, the size of the 3'-substitution is not limited by the pocket size of the enzyme's active site. Thus, in the amide and thiourea series, spacer length does not appear to have an effect on incorporation yield. This observed incorporation insensitivity to differences in the spacer-arm of the amide series is consistent with the suggestion that the furanose moiety in the Mn2+-nucleotides complex shows a conformation in which bulky substituents at the 3'-thiourea/amide are pushed away from the active site of the enzyme (S. Tabor et al., *Proc. Natl. Acad. Sci. USA*. 86:4076 (1988); D. Moras *Nature*, 364:572 (1993)).

D. Reporters

A wide variety of reactive forms of fluorescent dyes and other ligands are commercially available (from Fluka and Molecular Probe, for example) and are suitable reporters for the purposes of the molecules of the present invention. The choice of reporter depends in part on the possibility of fluorescence quenching through structural modification. Preferred pro-fluorescent reporters are those involving prototropic protons between pro-fluorescent and fluorescent configurations. Fluorescent dyes such as fluorescein, rhodamine, coumarin, ELF, and acridine are examples of particularly preferred reporters. Derivatives with known properties are preferably used in the design of pro-fluorescent structures.

For example, fluorescein analogs have hydroxyl groups as a prototypic regulator as well as COOH (fluorescent) vs. lactone (non-fluorescent) configurations. These key structural features allow fluorescein and its analogs to be used in 3'-PF-ddNTPs. In addition, fluorescein and its analogs (tetramethylrhodamine, ROX and Hex) are well studied in the argon-laser excitation system and have a good quantum yield. These dyes are released in a soluble form and can be detected, for example, by ultra-sensitive cytofluoro II on a variety of formatted substrates. As a result, fluorescein and its analogues are examples of preferred reporters in the design of 3'-PF-ddNTPs.

In other preferred molecules of the present invention, reporters are designed to be released in the form of a precipitate, thus allowing the resultant signal to be localized at the reaction site. This feature is particularly desirable, for example, in those embodiments utilizing a miniaturized chip format. In such embodiments, the reporter is preferably chosen to produce either a colored precipitate (as, for example, with BCIP/NBT) or a fluorescent precipitate (as in ELF and its analogs). Since fluorometric methods are potentially more sensitive than colorimetric methods, fluorogenic ELF and its analogs are examples of preferred reporters.

Fluorescence of ELF and its analogs are regulated by steric effects as discussed above. ELF substrates show almost no fluorescent background under either UV excitation or cytofluor reading. However, following enzymatic hydrolysis by phosphatase or esterase, ELF shows a strong fluorescence. Further, ELF precipitates can provide a resolution of less than 10 μm in ELISA or DNA chip-type assays.

Thorough purification of synthesized 3'-PF-ddNTPs is important, as contamination by unconjugated reporter molecules can potentially interfere with functional assays using 3'-PF-ddNTPs. Such purification may be, for example, by phase extraction, particularly where the free reporter and the nucleotide triphosphate conjugates have very different partition coefficiencies (solubility ratio in organic phase vs. aqueous phase). Generally, free reporters partition predominantly in an organic phase, while the triphosphate conjugates mainly partition in the aqueous phase. Phase extraction thus removes the unconjugated reporter molecules. A CHCl$_3$/Tris buffer solution is an example of a suitable system for phase extraction. Typically, the 3'-PF-ddNTP solution is mixed by vortexing and briefly centrifuged for phase separation. During periods of storage, there is some degradation of 3'-PF-ddNTP molecules. Consequently, 3'-PF-ddNTPs in solution are preferably stored in a two-phase storage solution. Free reporter molecules will partite into the CHCl$_3$ phase, leaving the aqueous phase substantially free of contaminating, unconjugated reporters. It should be noted that this separation is solubility dependent and applicable to highly lipophilic reporters. Other purification schemes for both lipophilic and non-lipophilic reporters will be readily apparent to those versed in the art.

II. Non-Gel-Based Microsequencing Methods of the Present Invention

In a preferred embodiment, a polymerase mediates the addition of a 3'-PF-ddNTP to the 3' end of an oligonucleotide that is hybridized to a target polynucleic acid. The pro-fluorescent label is subsequently removed from the 3'-PF-nucleotide, resulting in release of a fluorescent molecule. The label may be removed from the 3'-PF-ddNTP either chemically or enzymatically. Enzymatic removal of the fluorescent label is preferred however. In a particularly preferred embodiment, enzymatic removal of the label is accomplished by the same polymerase that mediates the addition reaction. Removal of the pro-fluorescent label from the 3'-PF-nucleotide results in the production of a detectable signal. Particular species of 3'-PF-nucleotides are preferably chosen such that the background fluorescence due to intact 3'-PF-nucleotides is acceptably low and the fluorescence produced by the free fluorescent label is detectably greater than that of the background. This allows for detection of a fluorescent signal due to 3'-PF-ddNTP incorporation without the prior removal of unincorporated 3'-PF-ddNTPs.

Individual reactions may be performed that comprise a single species of 3'-PF-ddNTP (3'-PF-ddATP, 3'-PF-ddTTP, 3'-PF-ddGTP, or 3'-PF-ddCTP). Alternatively, reactions may be performed where greater than one 3'-PF-ddNTP species is present. In a preferred embodiment of the methods of the present invention, all four 3'-PF-nucleotides are present simultaneously. In those embodiments where greater than one species of 3'-PF-nucleotide is present, fluorescent labels are preferably chosen such that at least one of the 3'-PF-nucleotide species is spectrally distinguishable from another. In those embodiments where reactions contain a single 3'-PF-nucleotide species, combinations of polymerase and 3'-PF-ddNTP species may be chosen such that the 3'-PF-ddNTP functions as either a terminator or a non-terminator nucleotide. Conversely, terminator nucleotides are preferably utilized in those embodiments wherein greater than a single 3'-PF-ddNTP species is used.

A. Oligonucleotide Primers

Oligonucleotide primers derived from a variety of sources may be used for the purposes of the present invention, either biologically or chemically derived. In embodiments utilizing a polymerase, enzyme, or enzyme combination with 3'→5' exonuclease activity, primer oligonucleotides are preferably used that are resistant to such 3'→5' exonuclease activity. Phosphorothiotated oligonucleotides are an example of a highly preferred type of exonuclease-resistant oligonucleotide primer suitable for the methods of the present invention. Oligonucleotides with phosphorothioate bonds at their 3' end are resistant to degradation by Taq polymerase (A. Skerra *Nucleic Acids Research* 20:3551–3554 (1992); H. P. Vosberg et al., *Biochemistry* 16:3633 (1977); C. M. de Noronha et al., *PCR Methods Appl* 2:131–6 (1992); T. Nikiforov U.S. Pat. No. 5,518,900). Another example of suitable oligonucleotide primers are those wherein deoxythymidine is replaced with C4-methyl-deoxythymidine in poly [d(A-T)], which renders the polymer resistant to the 3'→5' exonuclease activity of Klenow and T4 DNA polymerases.

Reaction conditions are preferably optimized to reduce biochemical noise. There are primarily two types potential biochemical noise, template dependant and template independent biochemical noise. Template dependant noise typically occurs as a result of false hybridization, priming, and extension of an oligonucleotide primer that is hybridized to a region of the target polynucleotide to which it is partially complementary. Specific oligonucleotides of sufficient length and complementarity and stringent hybridization conditions are therefore preferably used to reduce the occurrence of such template dependant noise.

The most common source of template independent noise occurs as a result of self-priming of the oligonucleotide primer. This typically occurs when the 3' end of an oligonucleotide primer self-hybridizes to another portion of the primer oligonucleotide and is extended during the extension reaction. Oligonucleotides are therefore preferably chosen wherein the 3' end of the oligonucleotide is not substantially complementary to another region of the oligonucleotide.

B. Solid-Phase vs. Solution-Phase

Solid supports are often used in in vitro assays to facilitate the removal of unutilized or unreacted substrates. An important aspect of the present invention is that 3'-PF-ddNTP incorporation or utilization is detectable in spite of the presence of unincorporated or unutilized 3'-PF-ddNTPs in solution. One implication of this is that methods of the present invention may be carried out either affixed to a solid support or in solution, with or without subsequent purification steps.

In those embodiments utilizing a solid support, a variety of substrates may be used. Suitable solid supports include, for example, materials constructed of glass, plastic, silicon, or paper. The support material may be fashioned into a bead, dipstick, test tube, membrane, sheet, chip, or a variety of other suitable shapes. In a preferred embodiment, the support will be a microtiter dish, having a multiplicity of wells. Conventional 96-well microtiter dishes used in diagnostic laboratories and in tissue culture are an example of a preferred support. The use of such a support allows the simultaneous determination of a large number of samples and controls, and thus facilitates the analysis. In addition, the use of such a support facilitates automation, which further enhances throughput. Automated delivery systems can further be used to provide reagents to such microtiter dishes. Similarly, spectrophotometric analysis of a multiplicity of wells may be simultaneously conducted using automated spectrophotometers. In another preferred embodiment, the solid support is a DNA chip, such as a derivatized glass slide, containing support-bound oligonucleotides spatially arranged in an array. The use of such a solid support potentially allows thousands of different polymerase-mediated primer extension reactions to be performed simultaneously.

C. Immobilization of Polynucleotides or Primer Oligonucleotides

In those embodiments where a solid-phase is preferred, either the primer oligonucleotides or the target polynucleotide may be affixed to a solid support. Further, the target polynucleotide or the primer nucleotides may be affixed to a solid support by a variety of suitable means, either covalent or non-covalent. Suitable means for immobilization are known in the art and will be compatible with either nucleic acid hybridization or polymerase-catalyzed primer extension reactions or both. A preferred means for immobilization is through a linker. A three carbon linker (Glen research) is an example of a highly preferred linker for such purposes, as the use of such linkers reduces the self-priming of the synthetic templates. Other suitable functional linkers may be used, however.

D. 3'-OH Exo-Cycling

Another important aspect of the present invention is that according to certain methods of the present invention, greater than one fluorophore may be released for each hybridized primer. In embodiments where a polymerase or other enzyme with 3'–5' exonuclease activity is used, the invention provides a novel means for amplifying the number of fluorescent molecules released, known as 3'-OH exo-cycling (FIG. 4). 3'-OH exo-cycling comprises three activities. They are: 1) The polymerase-mediated addition of a complementary 3'-PF-ddNTP to the end of an exonuclease-resistant oligonucleotide primer, 2) fluorophore release, and 3) exonuclease digestion back to the 3'-OH of the primer. The hybridized primer is then able to accept the polymerase-mediated addition of another 3'-PF-ddNTP. Thus, a cycle is formed that results in turnover of the complementary 3'-PF-ddNTP species. The order in which the activities occur may vary, so long as there is a substantial preference for the nucleotide species complementary to the base which lies 3' to an oligonucleotide primer that is hybridized to a target polynucleotide.

In a preferred embodiment of this aspect of present invention, polymerase activity, fluorophore release, and exonuclease digestion are all provided by separate enzymes or chemical treatments. One or more exonuclease-resistant oligonucleotides are preferably used. Suitable exonuclease-resistant oligonucleotides are known in the art and include, for example, phosphorothiotated primers. Polymerase-mediated addition of the 3'-PF-ddNTP that is complementary to the base adjacent to the 3'-OH of each hybridized primer is accomplished by any suitable enzyme or combination of enzymes with the appropriate polymerase activity.

Following polymerase-mediated addition of the 3'-PF-ddNTP, the fluorescent species of the fluorophore is released from the pro-fluorescent nucleotide with a suitable enzyme or combination of enzymes. Suitable enzymes may contain, for example, esterase, polymerase, alkaline phosphatase, or glycosidase activities.

Exonuclease-mediated digestion back to the exonuclease-resistant primer is provided by any suitable enzyme or combination of enzymes capable of regenerating the 3'-OH of the exonuclease-resistant primer. Exo-nuclease-III of *Escherichia coli* or T7 gene 6 are examples of suitable exonucleases.

In another preferred embodiment, both polymerase-mediated addition of the terminator nucleotide and removal of the fluorescent label will accomplished by the same enzyme or combination of enzymes. Removal of the fluorescent label may occur before, during, or after the addition of the 3'-PF-ddNTP. An example of a suitable polymerase is modified T7 DNA polymerase (Sequenase). In this embodiment of the present invention, if exonuclease activity is desired, one or more exonuclease-resistant primers are preferably used. When exonuclease activity is desired, it is provided by a separate enzyme or combination of enzymes that are capable of regenerating the 3'-OH of the exonuclease-resistant primer. Examples of suitable exonucleases are exonuclease-III of *Escherichia coli* or T7 gene 6.

In a particularly preferred embodiment, polymerase-mediated addition of the 3'-PF-ddNTP, release of the fluorescent label, and exonuclease activity are mediated by the same enzyme or combination of enzymes. Examples of preferred polymerases include, but are not limited to, T5 DNA polymerase or T7 DNA polymerase. In such an embodiment of the present invention, oligonucleotide primers are preferably used that are resistant to exonuclease activity. Suitable exonuclease-resistant oligonucleotides are known in the art and include, for example, phosphorothiotated primers.

Thus, in embodiments comprising a 3'-OH exo-cycle, enzymatic turnover of the 3'-PF-ddNTP results in an increased fluorescent signal. The polymerase repeatedly incorporates the complementary 3'-PF-ddNTP, removes the fluorescent label, and excises the newly incorporated terminator nucleotide. Removal of the fluorescent label may occur at any point in the process.

III. Methods for Sequence Detection or Detecting, Measuring, or Monitoring Polymerase Activity of the Present Invention The present invention is useful for monitoring the activity of a nucleic acid polymerase either in vitro or in vivo. For in vivo reactions, the 3'-linker of the 3'-PF-ddNTP preferably provides a hydrophobic region that is believed to facilitate cellular uptake for monitoring or detecting polymerase activity in vivo. Typically, one or more 3'-PF-ddNTP species is provided as a substrate or as part of a mixture of substrates for an in vitro or in vivo nucleic acid polymerase reaction. Upon polymerase activity, enzymatic hydrolysis of 3'-PF-ddNTPs occurs, thereby releasing a fluorescent moiety from the internally quenched or pro-fluorescent 3'-PF-ddNTP. The resultant fluorescence is detectable, for example, through the use of a variety of commercial fluorescence microplate readers. Thus, by means of including one or more species of 3'-PF-ddNTP during an in vitro or in vivo nucleic acid polymerase reaction, it may be determined whether the reaction has produced a product, i.e., whether nucleotides have been incorporated into a polynucleotide. Alternatively, a primer containing a terminal 3'-PF-ddNTP may be provided as a substrate. Hybridization of the primer is indicated release of the reporter as the polymerase cleaves the reporter in an attempt to "clean up" the base at the end of the primer so that another extension reaction can occur. Examples of particularly preferred embodiments include the monitoring of reactions or products from the polymerase chain reaction (PCR), random priming, nick translation, primer extension, reactions to fill in restriction site overhangs, reverse transcriptase reactions, detection of cellular polymerase activity, cellular DNA replication, etc.

The presently described 3'-PF-nucleotides are useful for all applications that use nucleotide triphosphates as substrates. This list is not meant to be exhaustive and it will be apparent to those skilled in the art that various substitutions and modifications may be made to the invention disclosed herein without departing from the scope and the spirit of the invention. The invention may be more easily understood by reference to the following examples.

EXAMPLES

Example 1

Fluorescence Detection in the Presence of Pro-fluorescence

An experiment is performed to demonstrate the feasibility of detecting fluorescence in the presence of pro-fluorescence. The fluorescence of the pro-fluorescent reporter fluorescein diacetate [F] is compared to that of fluorescein [F*] at concentrations ranging from 37.5 nmoles to 0.018 nmoles, in 2-fold serial dilutions. Fluorescence is read using a Cyto-II fluorescent reader at one cycle & one scan, filter excitation 485/20 and emission 530/25, gain 80%. Background fluorescence from the glass is 70. The results are shown in the table below. The diacetate is seen to be virtually non-fluorescent (pro-fluorescent) when compared to the same concentration of fluorescein over the range of concentrations shown.

| pmoles | 37.5 | 18.75 | 9.375 | 4.688 | 2.344 | 1.172 | 0.586 | 0.293 | 0.146 | 0.073 | 0.037 | 0.018 | bkg |
|---|---|---|---|---|---|---|---|---|---|---|---|---|---|
| [F*] | +++ | +++ | +++ | +++ | +++ | +++ | +++ | 72987 | 30531 | 17498 | 10608 | 10000 | 72 |
| {F} | 247 | 338 | 298 | 194 | 130 | 121 | 99 | 85 | 79 | 81 | 74 | 70 | 70 |

+++ Indicates the signal is beyond linear region for the instrument, too high to read accurately.

Example 2

Synthesis of a 3'-PF-ddNTP

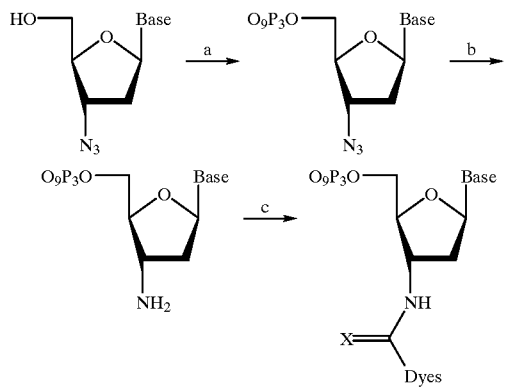

1a Base = T
1b Base = (ib) C
1c Base = G
1d BAse = (ib)A

The synthesis of intermediate 3'-amino ddNTPs has been reported. Below is an example of the synthesis of a Rhodamine isothiocyanate isomer.

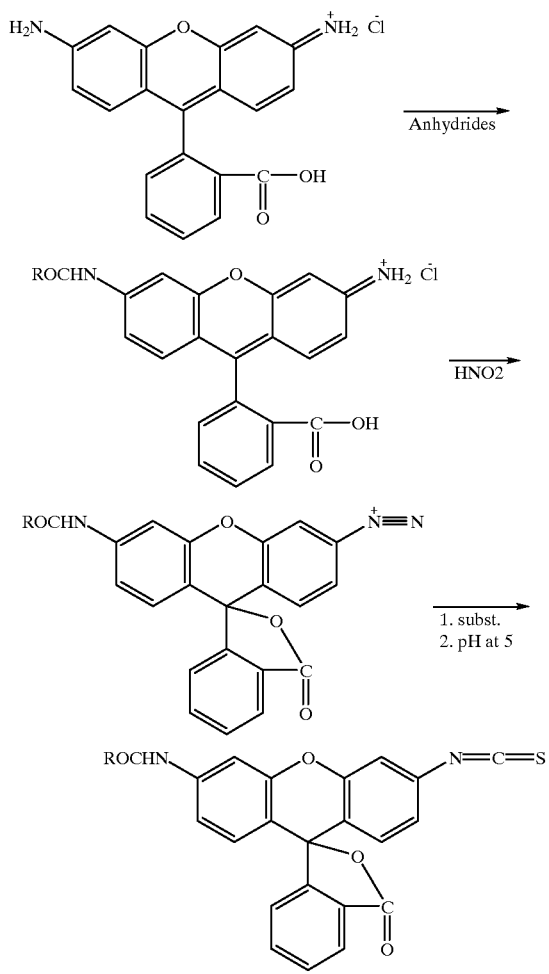

The commercially available starting material Rhodamine 110 is converted to mono amide by corresponding anhydrides. The diazonium salt is formed by reacting with $NaNO_2$ under acidic conditions. Under these conditions, the lactone is formed. The diazonium salt is very reactive and is readily converted to the active isothiocyanate form. The chemistry outlined has been used for derivatization of various isomers of fluorescein analogs. Amide linkages are prepared from activated esters of the dye and 3'-amino-ddNTPs.

Example 3

Synthesis of a 3'-PF-ddNTP

The target compound I is synthesized by a coupling reaction (Scheme III) between two key intermediates, the 3'-amino-2',3'-dideoxythymidine triphosphate (I-3 of Scheme I) and 3-acetamido-rhodamine-6-isocyanate (II-3 of Scheme II). The intermediates I-3 and II-3 are synthesized as shown in Schemes I and II below.

Synthesis of the intermediate I-3. The synthesis of 3'-$NH_2$-ddTTP (I-3) is performed according to scheme I, by means known in the art (R. E. Herreln et al., *Helvetica Chimca Acta* 77:586–596 (1994)) and described below. 3'-Azido-ddTTP (AZT, Wako Chemicals, Waco, Tex.) is phosphorylated with 2-chloro-4H-1,3,2-benzodioxa-phosphorin-4-one (J. Ludwig et al., *J. Org. Chem.* 54:631–635 (1989); J. A. Cade et al., *J. Chem. Soc.* 1249–1253 (1960)) followed by pyrophosphorylation. The resulting triphosphate (I-2) is purified by DEAE Sephadex ion exchange chromatography. The 3'-azido group of I-2 is then reduced to an amino group by a simple Staudinger reaction, using triphenylphosphine ($PPh_3$) in pyridine (M. Mag et al., *Nucleic Acids Res.* 17:5973–5988 (1989)), to yield I-3.

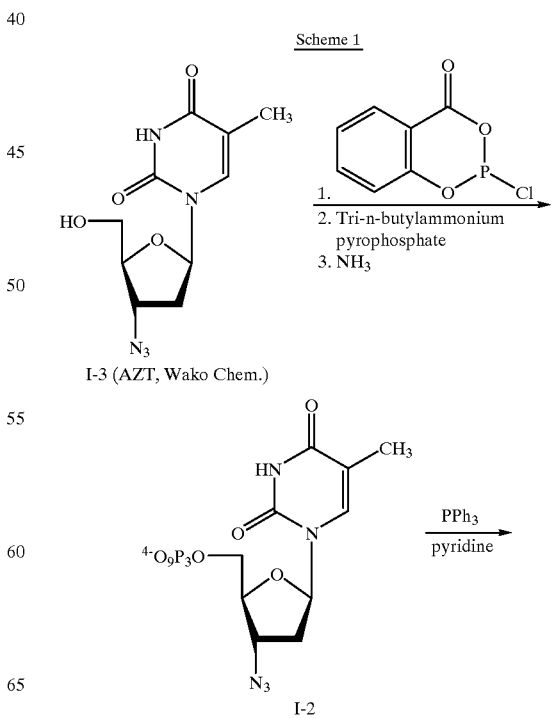

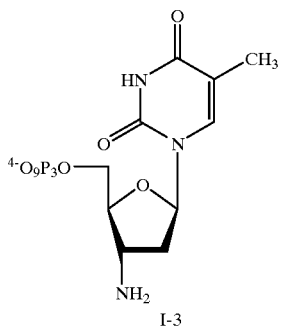

I-3

Synthesis of the intermediate II-3. The non-fluorescent dye intermediate II-3, possessing an activating functional group, is synthesized as outlined in scheme II, described below. Rhodamine 110 (II-1) is monoacetylated with neat acetic anhydride to give 3-acetamido rhodamine (II-2).

Alternately, the 3-amino group of rhodamine can also be selectively acylated by reaction with acetic acid in the presence of the peptide coupling reagent 1-(3-dimethylaminopropyl)-3-ethyl carbodiimide (EDC), using the procedure reported by Leytus et al. (S. P. Leytus et al., *Biochem. J.* 209:299–307 (1983)), for the synthesis of peptide-linked analogs of Rhodamine. The 6-amino group of II-2 is then converted to the isocyanate by one of two methods known in the art for such conversions. A mild, high-yielding method for the synthesis of aryl isothiocyanates reported by Mukaiyama et al. (T. Shibanuma et al., *Chem. Lett.* 573–574 (1977)) involves reaction of the aryl amine (II-2) with carbon disulfide and triethylamine (Et$_3$N) to yield the triethylammonium dithiocarbamate, which is treated with 2-chloro-N-methylpyridinium iodide and Et$_3$N at room temperature to yield the corresponding aryl isothiocyanate (II-3). Alternatively, the aryl amine is treated with thiophosgene and solid sodium bicarbonate in chloroform, according to a procedure reported by Uher et al. (M. Uher et al., *Coll. Czech. Chem. Commun.* 38:289–293 (1973)) to yield the aryl isothiocyanate (II-3).

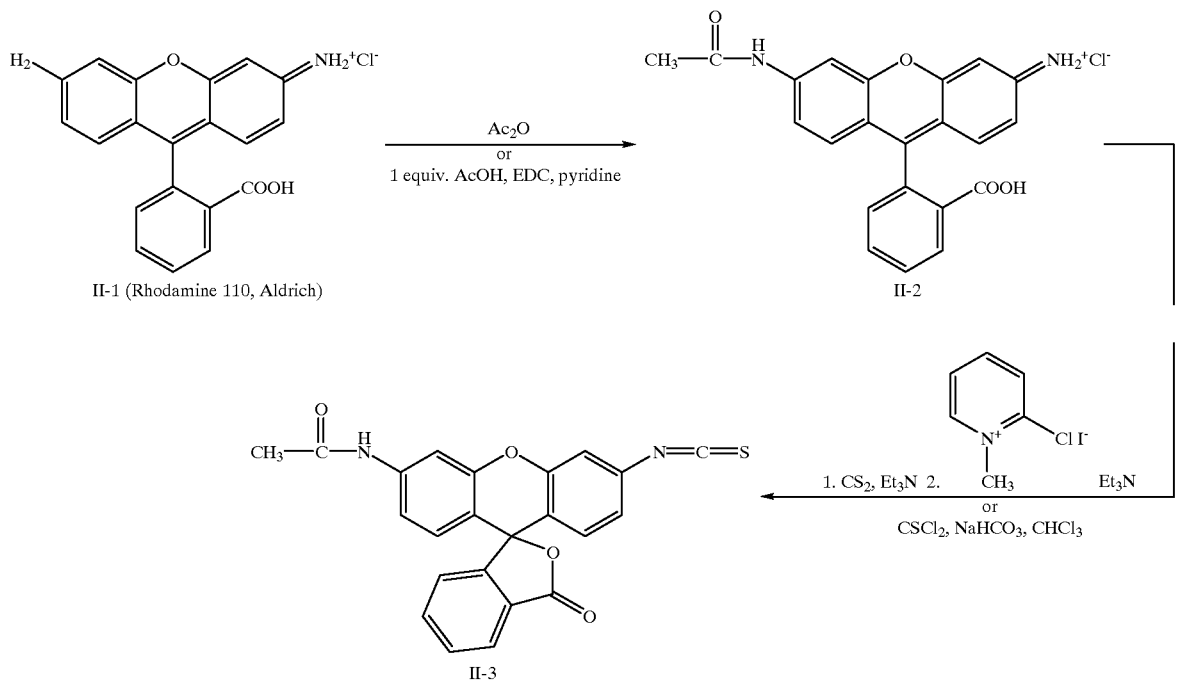

Scheme II

Production of Target I, from a coupling reaction between I-3 and II-3. I-3 and II-3 are then coupled according to scheme III, by a reaction of the 3'-amino group of I-3 with the isothiocyanate group of II-3. The reaction is carried out in a sodium bicarbonate buffer at pH 9.6, as described by Herreln et al.. The target compound I is then purified by DEAE Sephadex ion-exchange chromatography. The final compound is analyzed by $^1$H, $^{13}$C, and $^{31}$P NMR, mass spectroscopy, HPLC and elemental analysis.

primer oligonucleotide/target polynucleotide pairs are used to determine the specificity of incorporation of the complementary 3'-PF-ddNTP as compared to the non-specific incorporation of the non-complementary 3'-PF-ddNTPs. The ratio of the incorporation from each substrate is indicative of the incorporation specificity. This ratio is determined by a measurement, using a fluorescence reader or FluoroImager quantitation of the fluorescence resulting from each primer extension reaction product. In cases where the incor-

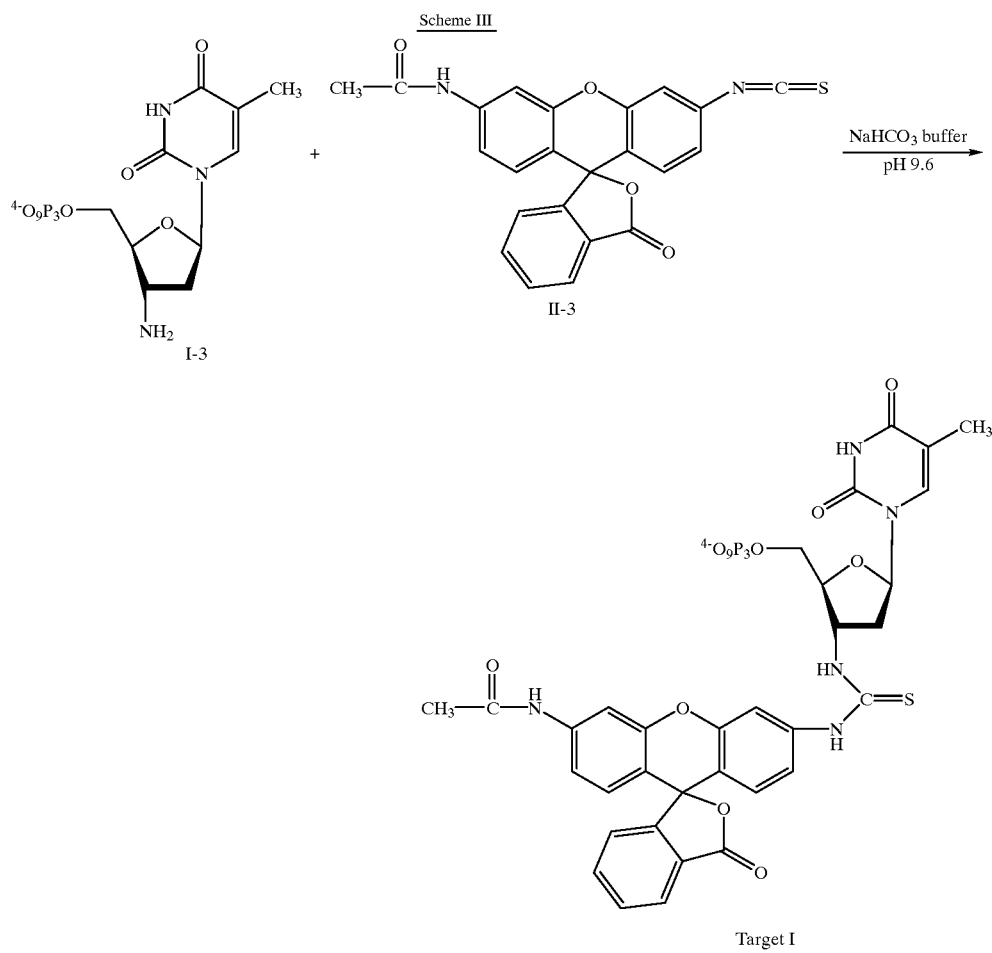

Scheme III

Target I

One difficulty in the synthesis of Target I is the low yield upon modification of rhodamine. The major difficulty is the unsymmetrical substitution of isothiocyanates required for conjugation to the 3'-amino nucleotide. Alternatively, acridine derivatives R-363 and H-6482 may be used (Molecular Probes, Inc.). Not only are they be easier to derivatize chemically, but they hydrolyze to give highly fluorescent compounds. In both cases, the preferred leaving group is a stable phenoxide anion. Both of these molecules exist in aqueous solution about pH 8 as anions, which have high extinction coefficients and absorption maxima, well separated from the neutral substrate. Conjugation to the 3'-OH of a nucleoside triphosphate may be accomplished, for example, through triphosphene, in order to prepare a carbonate [—OC(O)—O] type linkage.

Example 4
Determination of Fidelity and Specificity of 3'-PF-ddNTP Incorporation The aim of the functional assay is to determine the specificity/fidelity of the incorporation of 3'-PF-ddTTP. Four poration efficiency is low, a CCD/laser source excitation is used. The sensitivity of the CCD/laser source excitation set-up is such that it is able to detect the fluorescence resulting from as little as a few dye molecules. Templates are engineered so as to minimize self-priming. A 3-carbon linker (Glen research), which also functions to reduce self-priming, is used to affix the primer oligonucleotides to the solid support.

Except for the 3-carbon linker, GBA primer extension reactions are performed essentially as in Example 6C, below. $Mn^{2+}$, 3'-PF-ddNTP, primer oligonucleotide, and target polynucleotide concentrations are optimized to maximize specificity, fidelity, signal, and signal to noise ratio. Klenow fragment, modified sequenase, reverse transcriptase, and Taq-polymerase are each tested as polymerases in separate reactions.

Example 5
3'-OH Editing of a 3'-Modified Terminator

A variety of 3'-modified nucleotide triphosphates are tested as polymerase substrates in a gel-based GBA™

(single base primer extension) assay. The gel shift corresponds to 3'-amino-ddNTP incorporation, indicating that the extended primer does not have a bulky dye (tetramethylrhodamine), consistent with the results reported by Canard et al., regarding the editing properties of DNA polymerases. This gel behavior demonstrates that exo-Klenow also has catalytic editing properties, which cleave the amide bond and release the dye. Solid-phase based assays also demonstrate this activity, again indicating that catalytic hydrolysis of the 3'-amide occurs and therefore the extended primer does not contain tetramethylrhodamine.

Example 6

Genetic Bit Analysis with a 3'-PF-ddNTP

In order to demonstrate the feasibility of adapting GBA technology to the use of 3'-PF-ddNTP nucleotide species, the following PF-GBA experiments are performed:

A. Solution Phase GBA Using a 3'-PF-ddNTP

Peripheral blood lymphocytes (PBL) are isolated from human whole blood by ficol/hypaque centrifugation. Genomic DNA is isolated from PBL using the SDS/Proteinase K procedure (Maniatis, T. Molecular Cloning, A Laboratory Manual, Cold Spring Harbor Laboratory Press, Cold Spring Harbor, 1989). Target DNA is amplified by PCR from total genomic DNA. PCR primers for amplifying regions comprising a panel of human genome markers, as well as genetic disease markers for cystic fibrosis, cardiovascular disease, and p53 are used. Exonuclease-resistant phosphorothioated oligonucleotides complementary to these regions are prepared by solid-phase synthesis according to the methods of Skerra, Vosberg et al., and Noronha et al. (A. Skerra *Nucleic Acids Research* 20:3551–3554 (1992); H. P. Vosberg et al., *Biochemistry* 16:3633(1977); C. M. de Noronha et al., *PCR Methods Appl* 2:131–6 (1992); T. Nikiforov U.S. Pat. No. 5,518,900).

In a 96-well tissue culture dish, 10 μl of the target DNA in hybridization buffer is added to each well of the tissue culture dish. 10 μl of one of the oligonucleotide solutions in hybridization buffer is also added to each well. Several wells are reserved for mock, no primer oligonucleotide, and no target DNA controls. The dish is covered and incubated at 55° C. for 30 minutes to allow hybridization. 20 μl of a polymerase extension mix, containing ddATP, ddCTP, ddGTP, a 3'-PF-ddTTP, MnCl$_2$, and T7 DNA polymerase is then added to the wells and the reaction is incubated at room temperature. Fluorescence intensity is measured at 0, 5, 10, 30, and 60 minutes.

B. Target Immobilized GBA Using a 3'-PF-ddNTP

Target DNA is isolated from PBL essentially as above and immobilized to each well of a 96-well tissue culture dish. 20 μl of oligonucleotide solution in hybridization buffer is added to the wells. The dish is covered and incubated at 55° C. for 30 minutes to allow hybridization of the oligonucleotides to the immobilized target nucleic acid. Several wells are reserved for mock, no primer oligonucleotide, and no target DNA controls. The wells are washed, 20 μl of a polymerase extension mix, containing ddATP, ddTTP, ddGTP, a 3'-PF-ddCTP, MnCl$_2$, and T7 DNA polymerase is then added to the wells 1–7 and the reaction is incubated at room temperature. Fluorescence intensity is measured at 0, 5, 10, 30, and 60 minutes.

C. Primer Immobilized GBA Using a 3'-PF-ddNTP

Exonuclease-resistant phosphorothioated oligonucleotides are prepared as above and amino-derivatized at their 5' end, using Aminolink 2 (Applied Biosystems) according to the manufacturer's recommendations. 5'-amino-modified, exonuclease-resistant oligonucleotides are then covalently coupled to wells of a 96-well dish (Nunc) by incubating the 5'-amino modified, exonuclease-resistant oligonucleotides in 50 μl of 3mM sodium phosphate buffer, pH 6, 20 mM 1-ethyl-3-(3-dimethylaminoproply)-carbodiimide (EDC) overnight at room temperature. After coupling, the plate is washed three times with 10 mM Tris pH 7.5/150 mM NaCl 0.05% Tween-20. 20 μl of hybridization buffer is added to well 1. 20 μl of target DNA solution in hybridization buffer is added to the wells. Several wells are reserved for mock, no primer oligonucleotide, and no target DNA controls. The dish is covered and incubated at 55° C. for 30 minutes to allow hybridization of the target DNA to the immobilized oligonucleotides. The wells are washed, 20 μl of a polymerase extension mix, containing ddATP, ddTTP, ddGTP, a 3'-PF-ddCTP, MnCl2, and T7 DNA polymerase is then added to the wells and the reaction is incubated at room temperature. Fluorescence intensity is measured at 0, 5, 10, 30, and 60 minutes.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A compound of formula (I):

wherein N represents a nucleotide; L$_1$ represents a cleavable linking group, wherein one end of said cleavable linking group is attached to the 3' position of said nucleotide; L$_2$ represents a spacer linking group; and Reporter represents a chromophore or a pro-flourescent fluorophore, wherein said Reporter exhibits substantially greater fluorescence when uncoupled from said compound.

2. The compound according to claim 1, wherein L$_1$ is at least one moiety selected from the group consisting of: NH—C(O)—, NH—C(S)—, CH$_2$CO, O—C(O)—, or —OPO$_3$—.

3. The compound according to claim 1, wherein L$_2$ is at least one moiety selected from the group consisting of: —(NH—CO)$_n$— or —(OCH$_2$—CH$_2$)$_n$.

4. The compound according to claim 3, wherein L$_1$ is at least one moiety selected from the group consisting of: NH—C(O)—, NH—C(S)—, CH$_2$CO,O—C(O)—, or —OPO$_3$—.

5. The compound according to claim 4, wherein Reporter is selected from the group fluorescein, rhodamine, coumarin, acridine, and ELF.

6. A method for determining the identity of a nucleotide at at least one preselected site in a target polynucleotide, said method comprising the steps of:

(a) incubating a target polynucleotide in the presence of at least one primer oligonucleotide, said primer having a sequence complementary to a sequence immediately 3' to said preselected site of said target polynucleotide, said incubation being under conditions sufficient to permit said primer oligonucleotide to hybridize to said target oligonucleotide and to thereby form a hybridized product;

(b) further incubating said hybridized product in the presence of a mixture comprising a polymerase and at least one pro-fluorescent nucleotide species; said incubation being under conditions sufficient to permit the polymerase-mediated template-dependent addition of said nucleotide species onto the 3'-terminus of said hybridized primer oligonucleotide;

(c) permitting said polymerase to mediate the template-dependant addition of a pro-fluorescent nucleotide species onto the 3'-terminus of said hybridized primer oligonucleotide, said addition being additionally dependant on said mixture containing a pro-fluorescent nucleotide species that is complementary to a nucleotide present at said preselected site;

(d) permitting the enzymatic hydrolysis of a reporter from said complementary pro-fluorescent nucleotide species; and (e) determining the identity of said nucleotide at said preselected site from the identity of said reporter.

7. The method of claim 6, further comprising multiple iterations of steps (b), (c), and (d), prior to step (e).

8. The method of claim 7, wherein said mixture in step (b) contains a single species of pro-fluorescent nucleotide and said species is a terminator or non-terminator pro-fluorescent nucleotide species.

9. The method of claim 7, wherein said mixture in step (b) contains greater than one distinguishable species of pro-fluorescent nucleotide and said species are terminator pro-fluorescent species.

10. The method of claim 6, wherein said mixture in step (b) contains greater than one species of pro-fluorescent nucleotide and said species are terminator pro-fluorescent nucleotide species.

11. The method of claim 6, wherein said pro-fluorescent nucleotide species are 3'-PF-ddNTP species.

12. The method of claim 11, wherein a multiplicity of said primer oligonucleotides are spatially arranged in an array, said array having one or more elements, said elements being at least 1 μM in diameter.

13. The method of claim 12, wherein said primer oligonucleotides are affixed to a solid support.

14. The method of claim 12, wherein said target polynucleotide is affixed to each array position of a solid support.

15. The method of claim 6, wherein in step (d) said hydrolysis of said reporter substantially unquenches the fluorescence of said reporter.

16. The method of claim 6, wherein said target polynucleotide is a DNA molecule.

17. The method of claim 6, wherein said target polynucleotide is an RNA molecule and said polymerase is a reverse transcriptase.

18. The method of claim 6, wherein in step (d) said enzymatic hydrolysis of said reporter is accomplished by said polymerase.

19. The method of claim 6, wherein said polymerase is a DNA polymerase, or an RNA polymerase, or a reverse transcriptase.

20. The method of claim 19, wherein said polymerase is a eukaryotic DNA polymerase.

21. The method of claim 19, wherein said polymerase is a prokaryotic DNA polymerase.

22. The method of claim 6, wherein said polymerase is a thermostable polymerase.

23. The method of claim 6, wherein said polymerase is Taq polymerase or Taq-related polymerase.

24. The method of claim 6, wherein said polymerase is a T7 DNA polymerase.

25. The method of claim 6, wherein said polymerase is a modified T7 DNA polymerase.

26. The method of claim 6, wherein said polymerase is a T5 DNA polymerase.

27. The method of claim 6, wherein said polymerase is a Klenow Class DNA polymerase.

28. The method of claim 22, wherein said polymerase is a T5 DNA polymerase.

29. The method of claim 22, wherein said polymerase is T7 DNA polymerase.

30. The method of claim 18, wherein said polymerase is a modified T7 DNA polymerase.

31. A method for determining the nucleic acid sequence of a target polynucleotide, said method comprising the steps of:

(a) incubating a target polynucleotide in the presence of at least one primer oligonucleotide, said primer oligonucleotide having a sequence complementary to a sequence immediately 3' to a first preselected site of said target polynucleotide, said incubation being under conditions sufficient to permit said primer oligonucleotide to hybridize to said target oligonucleotide and to thereby form a hybridized product;

(b) further incubating said hybridized product in the presence of a mixture comprising a polymerase and at least one terminator pro-fluorescent nucleotide species; said incubation being under conditions sufficient to permit the polymerase-mediated template-dependant addition of said terminator pro-fluorescent nucleotide species onto the 3'-terminus of said hybridized primer oligonucleotide;

(c) permitting said polymerase to mediate the template-dependant 3' extension of said primer oligonucleotide by one terminator pro-fluorescent nucleotide species, said extension being additionally dependant on said mixture containing a terminator pro-fluorescent nucleotide species that is complementary to a nucleotide of the target polynucleotide present at said preselected site;

(d) permitting the enzymatic hydrolysis of a reporter from said complementary nucleotide species, thereby restoring a 3' end suitable for the polymerase-mediated template-dependant extension of a said primer oligonucleotide by an additional terminator pro-fluorescent nucleotide species;

(e) determining the identity of said nucleotide at said preselected site from the identity of said hydrolyzed reporter;

(f) performing multiple iterations of steps (b) through (e), thereby in each iteration sequentially extending said primer oligonucleotide by one terminator pro-fluorescent nucleotide, and determining the identity of a next adjacent nucleotide of said target polynucleotide from the identity of said hydrolyzed reporter.

32. The method of claim 31, wherein the hydrolyzed reporter is removed by washing between each iteration of steps (b) through (e).

33. The method of claim 31, wherein in step (d) said hydrolysis of said reporter substantially unquenches the fluorescence of said reporter.

34. The method of claim 31, wherein said target polynucleotide is a DNA molecule.

35. The method of claim 31, wherein said target polynucleotide is an RNA molecule and said polymerase is a reverse transcriptase.

36. The method of claim 31, wherein in step (d) said enzymatic hydrolysis of said label is accomplished by said polymerase.

37. The method of claim 31, wherein in step (d) said enzymatic hydrolysis of said label is accomplished by an enzyme with an activity selected from the group: esterase, alkaline phosphatase, or glycosidase.

38. The method of claim 31, wherein said terminator pro-fluorescent nucleotide species are 3'-PF-ddNTP species.

39. The method of claim 31, wherein said polymerase is a T7 DNA polymerase.

40. The method of claim 31, wherein said polymerase is a modified T7 DNA polymerase.

41. The method of claim 31, wherein said polymerase is a T5 DNA polymerase.

42. The method of claim 31, wherein said polymerase is a Klenow Class DNA polymerase.

43. The method of claim 36, wherein said polymerase is a T5 DNA polymerase.

44. The method of claim 36, wherein said polymerase is T7 DNA polymerase.

45. The method of claim 36, wherein said polymerase is a modified T7 DNA polymerase.

46. A method for detecting a reporter comprising the steps of
 (a) providing in a reaction a 3'-PF-ddNTP species and an enzyme, such that said 3'-PF-ddNTP is utilized as a substrate in the reaction catalyzed by said enzyme, thereby hydrolyzing the reporter of said 3'-PF-ddNTP species,
 said 3'-PF-ddNTP species being of the formula N—$L_1$—$L_2$-Reporter, wherein N represents a nucleotide; $L_1$ represents at least one cleavable linking group selected from the group consisting of NH—C(O)—, NH—C(S)—, $CH_2CO$, O—C(O)—, or —$OPO_3$—, wherein one end of said cleavable linking group is attached to the 3' position of said nucleotide; $L_2$ represents at least one spacer linking group selected from the group consisting of: —(NH—CO)$_n$— or —(OCH$_2$—CH$_2$)$_n$; Reporter represents a chromophore or a pro-fluorescent fluorophore; and
 (b) detecting said hydrolyzed reporter.

47. The method of claim 46, wherein said enzyme is a polymerase.

48. The method of claim 46, wherein said reporter is a reporter is selected from the group fluorescein, rhodamine, coumarin, acridine, and ELF.

49. A method for determining cell viability that comprises the steps of:
 (a) providing to a 3'-PF-ddTNP species to a cell, such that hydrolysis of a reporter from said 3'-PF-ddNTP is dependant upon the viability of said cell,
 said 3'-PF-ddNTP species being of the formula N—$L_1$,—$L_2$-Reporter, wherein N represents a nucleotide; $L_1$ represents at least one cleavable linking group selected from the group consisting of NH—C(O)—, NH—C(S)—, $CH_2CO$, O—C(O)—, or —$OPO_3$—, wherein one end of said cleavable linking group is attached to the 3' position of said nucleotide; $L_2$ represents at least one spacer linking group selected from the group consisting of: —(NH—CO)$_n$— or —(OCH$_2$—CH$_2$)$_n$; Reporter represents a chromophore or a pro-fluorescent fluorophore; and
 (b) detecting said hydrolyzed Reporter.

* * * * *